US010870069B2

(12) United States Patent
Stantchev

(10) Patent No.: US 10,870,069 B2
(45) Date of Patent: Dec. 22, 2020

(54) SUPERHEATED WATER EXTRACTION WITH COUNTERPRESSURE SYSTEM AND METHOD THEREOF

(71) Applicant: George Stantchev, Phoenix, AZ (US)

(72) Inventor: George Stantchev, Phoenix, AZ (US)

(*) Notice: Subject to any disclaimer, the term of this patent is extended or adjusted under 35 U.S.C. 154(b) by 272 days.

(21) Appl. No.: 15/857,893

(22) Filed: Dec. 29, 2017

(65) Prior Publication Data

US 2018/0185768 A1 Jul. 5, 2018

Related U.S. Application Data

(60) Provisional application No. 62/441,273, filed on Dec. 31, 2016.

(51) Int. Cl.
*B01D 11/02* (2006.01)
*A61K 36/00* (2006.01)

(52) U.S. Cl.
CPC .......... *B01D 11/0288* (2013.01); *A61K 36/00* (2013.01); *A61K 2236/331* (2013.01); *B01D 11/0203* (2013.01); *B01D 11/028* (2013.01); *B01D 11/0292* (2013.01)

(58) Field of Classification Search
CPC ............ B01D 11/0257; B01D 11/0288; B01D 11/0203; B01D 11/028; B01D 11/0292; B01D 11/027; B01D 11/0253; A61K 36/00; A61K 2236/331; A61K 2236/30; A61K 2236/50; A61K 2236/55
See application file for complete search history.

(56) References Cited

U.S. PATENT DOCUMENTS

| | | | | | |
|---|---|---|---|---|---|
| 3,064,018 | A | * | 11/1962 | Verrando Bruera | ...... C11B 1/10 554/11 |
| 4,929,462 | A | * | 5/1990 | Moorman | .......... B01D 11/0203 426/478 |
| 5,902,396 | A | * | 5/1999 | Purdy | ..................... C30B 23/00 117/71 |
| 6,001,256 | A | * | 12/1999 | Hawthorne | ............... B09C 1/02 210/633 |

(Continued)

FOREIGN PATENT DOCUMENTS

WO WO-2016107824 A1 * 7/2016 ............. C01G 21/12

OTHER PUBLICATIONS

Basile et al. Extraction of Rosemary by Superheated Water. J. Agric. Food Chem. 1998, 46, 5205-5209. (Year: 1998).*

(Continued)

*Primary Examiner* — Katherine Zalasky McDonald

(57) ABSTRACT

This invention discloses an apparatus for extraction of constituents with extraction fluid present in a substance by means of an extraction fluid constituted by a water heated to high temperature known as super-heated water (SHW). According to this invention, in the heater the water is heated to a subcritical point and introduced to the extractor contacting takes place between the substance and the extraction fluid to dissolve the constituents in the fluid. The fluid leaving the extractor is then cooled in a cooler. The process is performed under constant counter pressure given by a Nitrogen tank. Separation of the volatile components is done in one or multistage countercurrent liquid-liquid system with any volatile solvent with proper solubility of the constituents or in a distillation column. distillation column.

13 Claims, 5 Drawing Sheets

(56) References Cited

U.S. PATENT DOCUMENTS

| | | | |
|---|---|---|---|
| 2005/0148088 A1* | 7/2005 | Ong | C07H 15/256 436/96 |
| 2007/0014912 A1* | 1/2007 | Mazza | A23L 5/44 426/615 |
| 2007/0175927 A1* | 8/2007 | Ozanne | F04B 43/113 222/334 |
| 2009/0166175 A1* | 7/2009 | Waibel | B01D 3/40 203/49 |
| 2015/0119592 A1* | 4/2015 | Hamler | C11B 1/10 554/16 |
| 2015/0157958 A1* | 6/2015 | Mazza | B01D 11/0207 422/618 |
| 2015/0375136 A1* | 12/2015 | Swan | C11B 9/027 202/170 |
| 2017/0002292 A1* | 1/2017 | Cumings | B01D 11/028 |
| 2017/0113161 A1* | 4/2017 | Stantchev | B01D 3/10 |
| 2017/0355655 A1* | 12/2017 | Lange | C10G 21/12 |

OTHER PUBLICATIONS

Gogus et al. Superheated Water Extraction of Essential Oils of Origanum micranthum. Journal of Chromatographic Science, vol. 43 , Feb. 2005, 87-91. (Year: 2005).*

Ilvesniemi et al. Pressurized hot water flow-through extraction system scale up from the laboratory to the pilot scale. Green Chem., 2014, 16, 3186-3194. (Year: 2014).*

Mohan et al. Pressurized Hot Water Extraction. International Journal of Latest Trends in Engineering and Technology (IJLTET). vol. 4 Issue 4 Nov. 2014, 25-30. (Year: 2014).*

Smith, Roger. Extractions with superheated water. Journal of Chromatography A, 975 (2002) 31-46. (Year: 2002).*

Teo et al. Pressurized hot water extraction (PHWE). Journal of Chromatography A, 1217 (2010) 2484-2494. (Year: 2010).*

* cited by examiner

SUPERHEATED WATER EXTRACTION WITH COUNTERPRESSURE SYSTEM AND METHOD THEREOF

This non-provisional application claims priority claim under 35 U.S.C. § 119(e) on U.S. Provisional Application No. 62/441,273, filed Dec. 31, 2016, the entire contents of which are incorporated herein by reference.

FIELD OF THE INVENTION

The present invention relates to a water based extraction system and method thereof for extracting at least one constituent in a substance by an extraction fluid substituted by a super-heated water.

BACKGROUND

The process of extraction of plant materials is a mass-exchange process of a passage of certain constituents thereof to a liquid solvent. The type of substances throughput depends on the selectivity of the solvent used. It is defined by the principle of "similar substances are dissolved in similar solvents", as under similar understood substances and solvents with similar values in their dielectric constant value. Based on this principle, for example, using water as a solvent with dielectric constant of 80.4, only water-soluble substances are extracted with dielectric constants close to this value. With alcohol as a solvent with a dielectric constant of 25.0, only alcohol soluble constituents with dielectric constants around this value are extracted and by hexane with a dielectric constant of 2.0, only oil soluble substances are extracted with similar values.

Referring to FIG. 1, the dielectric constant (vertical axis) vs. water-alcohol concentration in % (horizontal axis) is shown for ethanol at temperatures 20, 40, 50, 60 and 80% (top down charts). The trend is to decrease the dielectric constant while increasing temperature and concentration.

Referring to Table 1, depending on the desired composition and quality of the extract to be obtained, an appropriate type of solvent needs to be selected. It is found that a solvent dielectric constant depends significantly on the temperature. Thus, for water at 20° C. the dielectric constant is 80.4, at 100° C. it is 55.4, and at 200° C. decreases to a value of 34.6. In this regard, the dielectric constant of pure water at 170° C. is equal to that of 67% water-alcohol solution which at 20° C. is 39.9.

For water heated to 260° C., the dielectric constant is 25.30. In this regard, the dielectric constant of pure water at 260° C. is equal to that of 100% alcohol at 20° C. This allows the solvent to be substituted by water under pressure and temperatures in the range 100-300° C. to obtain oil-soluble and alcohol-soluble components from plant materials.

Referring to FIG. 2, the extraction time lowers with higher temperature. Extraction time of 70 seconds will be sufficient at 200° C. for extraction, while it will be 10 minutes at 140° C. and 35 minutes at 100° C.

TABLE 1

| Temperature, ° C. | 20 | 40 | 50 | 60 | 80 | 100 | 150 | 200 | 250 | 300 |
|---|---|---|---|---|---|---|---|---|---|---|
| Dielectric Constant, water | 80.37 | 73.12 | 69.85 | 66.62 | 60.58 | 55.40 | 43.90 | 34.60 | 27.46 | 19.66 |
| Dielectric Constant, 100% alcohol | 25.00 | 22.20 | 20.87 | 19.55 | | | | | | |
| Dielectric Constant, 80% alcohol | 35.00 | 30.00 | 28.00 | 26.00 | 24.00 | | | | | |

SUMMARY

It is one objective of the present invention to provide an extraction system. At least one constituted of a substance can be extracted under a relative low or mid pressure and there is no need to change pressure under the extraction process. A super-heated water as a solvent will be used, therefore the users can perform the extraction process with reasonable costs.

For achieving above objective, the present invention provides an extraction apparatus, which introduces super-heated water as an extraction fluid. It comprises an extractor, a cooler unit, an air tank and a heater. The extraction apparatus extracts at least one constituent in a substance by dissolving the constituent (or constituents) in the extraction fluid under pressure and temperature and then cooling the extraction fluid and the constituent (or constituents) dissolved in the extraction fluid and separating the said fluid from constituents by various means. Therefore, the constituent (or constituents) and the extraction fluid can be separated.

The first level separation is performed in the cooler/decanter (2) where the oily components will separate on the top due their lighter mass and the remaining fluid will remain. The non-volatile particles and the collective mixture is called miscella. The non-volatile particles can be separated with other means for example liquid to liquid extraction using other food grade or organic solvents.

The processes usually perform under constant low pressure at around 12 bar and variable considerably high temperature around 170° C. allowing the extraction fluid to go through a dielectric constant change to match the constant at the target constituents to be extracted and separate the extracted constituents (extract).

Throughout the remainder of the present invention, the term "extraction fluid" will mean that it is a subcritical fluid or pressurized liquid under the aforementioned temperature and pressure conditions also called solvent. The term "substance" will refer to a source material and the term "extracted constituents" as targeted extraction materials in substance or in brief referred as an extract. The term "miscella" will refer to a rare solvent/extract mixture with the substance or substances.

It is one object of the present invention to provide an extraction method. At least one constituted of a substance can be extracted under a relative low or mid pressure and there is no need to change pressure under the extraction process. A super-heated water as a solvent will be used, therefore the users can perform the extraction process with reasonable costs.

Table 1 is a relation chart of water temperature with water dielectric constant, 100% alcohol dielectric constant and 80% alcohol dielectric constant.

Figure 1:
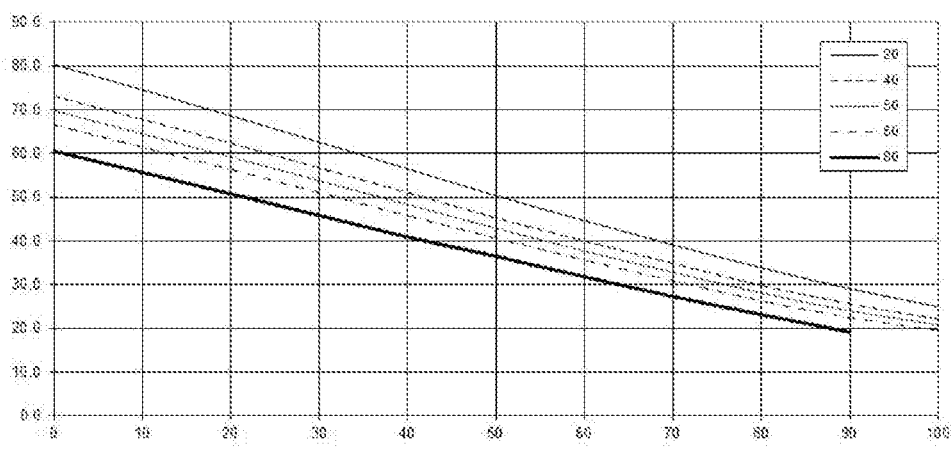
FIG. 1 is a dielectric constant (vertical axis) vs. water-alcohol concentration in % (horizontal axis) is shown for ethanol at temperatures 20, 40, 50, 60 and 80% (top down charts). The trend is to decrease the dielectric constant while increasing temperature and concentration.
Figure 2:
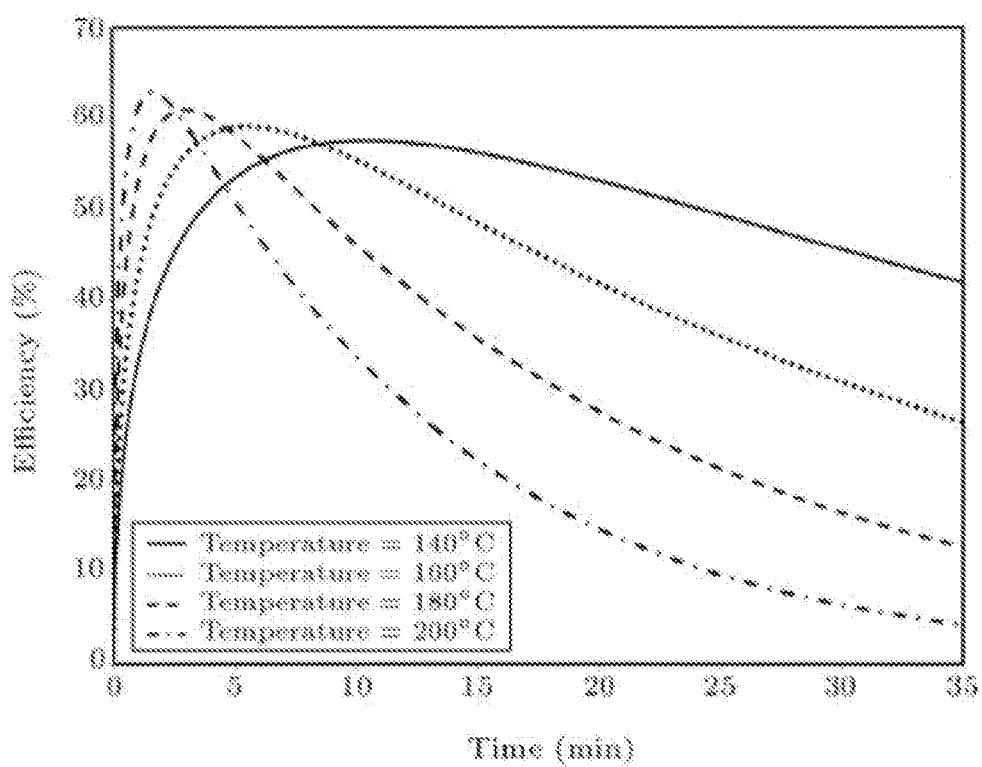

FIG. 2 is a line chart of time (minutes) and efficiency (%) when water temperature at 140° C., 160° C., 180° C., 200° C.

Figure 3:
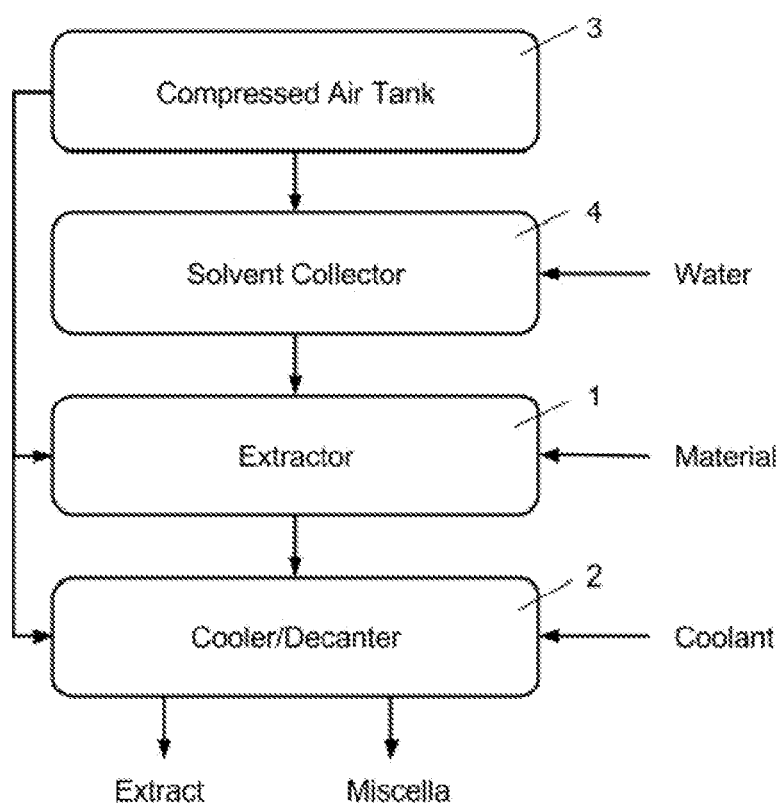

FIG. 3 is a process block diagram of present invention.

Figure 4:
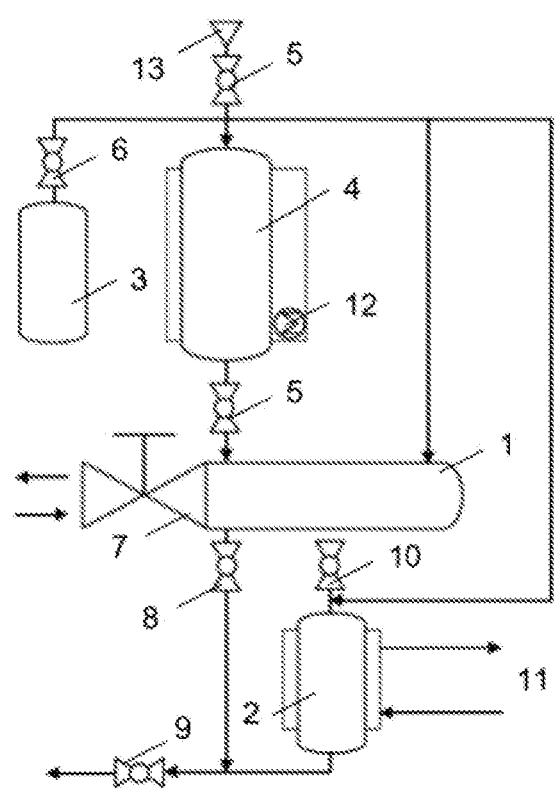

FIG. 4 is a block diagram of a portable extraction device according to the present invention.

Figure 5:
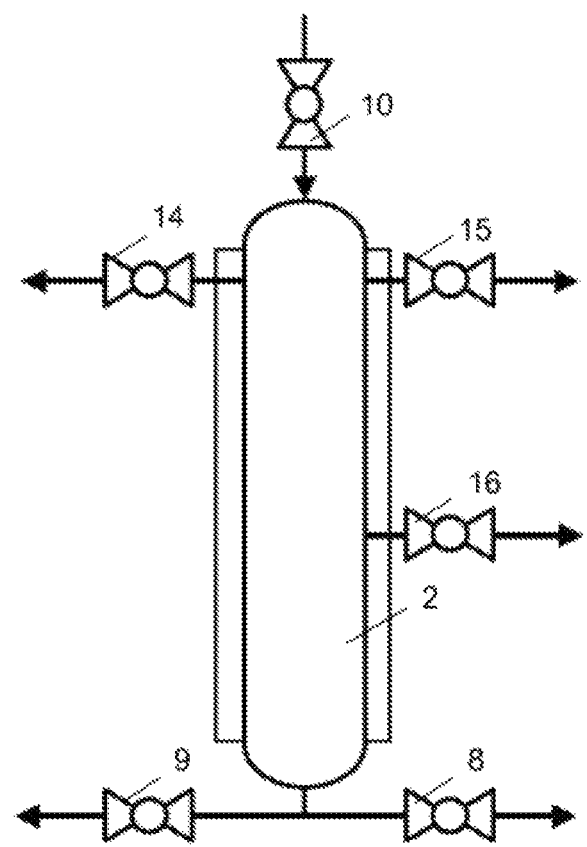

FIG. 5 is a structural diagram of an extractor device according to the present invention.

DETAILED DESCRIPTION OF THE PREFERRED EMBODIMENTS

In order to carry out this type of extraction, the substance containing the constituents to be extracted is generally introduced into an extractor (1) and in the latter, is brought into contact with an extraction fluid raised to the desired temperature and pressure within the same extractor vessel. On leaving the extractor, the extraction fluid contains certain constituents and efficiently separates the extracted constituents in sequential processes.

The present invention therefore relates to a process for the extraction of at least one constituent present in a substance by means of an extraction fluid constituted by a super-heated water comprising contacting said substance with said fluid in an extractor at a temperature T and a pressure P adequate for dissolving the constituent or constituents in said fluid, then separating the constituent or constituents extracted in said fluid, characterized in the separation process of said extracted constituent or constituents.

The system diagram according to the invention is shown at FIG. 3. A perforated basket with the material to be extracted is introduced to the extractor (1). The solvent, distilled water, is heated in a collection vessel called a heater (4) via electric heater to the required temperature for extraction. Then super-heated water is introduced to the extractor and left with the material for a certain time in order to dissolve the necessary substances. After the time for extraction the miscella is collected in a vessel called cooler (2), where it is cooled down to desired temperature in order to lower the degradation of material.

In the cooled mixture, there is a presence of oil fraction lighter than the water that forms the top layer and separates by weight, the rest of the solution is drained from the bottom of the container. To avoid boiling of the water solvent, a counter pressure is maintained by either carbon dioxide or nitrogen cylinder (3). The drained and cooled solvent further can be extracted in liquid-liquid process or vacuum evaporated for concentrating the resultant constituent and further drying to a powder stage.

Referring to FIG. 4, the example extraction process is as follow: Feed raw material basket in extractor by opening and closing valve (7). Open valve (5) and load demineralized water in heater (4) via the loading pipe (13) then close loading valve (5). Open valve (6) to let the pressurized gas (nitrogen) from tank (3) fill the entire system. After system pressure reaches set value close valve (6). Switch-on the electric heater (12) to heat-up solvent in the water heater (4).

When the water temperature in the heater (4) reaches the set extraction temperature, switch off the electric heater (12). Open valve (5) and let the solvent in the extractor (1) already loaded with material. After the time for extraction is up, close valve (5) and open valve (8) to let miscella drain in cooler (2). The cooler is constantly cooled by circulating coolant (11). The process continues until the miscella is cooled and the valve (10) is opened to release the nitrogen. The volatile oil extract is separated from the miscella in the cooler (2) and the remaining miscella is drained via valve (9). The material is removed from the extractor (1) by opening valve (7). For multiple extractions follow the process above from the beginning.

The current invention apparatus is constructed by the following elements: hot water heater, extractor, cooler/decanter, gas tank and a supporting frame. The system uses a gravitational flow for lowest cost equipment and vessels are situated in space as on FIG. 3. The nitrogen can be recirculated by installing vacuum pumps at each vessel (not shown). The elements are explained as follows.

Extractor 1 is a vertical or horizontal cylindrical vessel that is used for collecting the raw plant material and carrying out the extraction process. The example total volume may be 2.6 liter, with useful volume of 1.7 liter. It is situated in the middle part of the system in order to ensure gravity flow of the hot solvent from the heater (4) to the extractor (1). The extractor (1) is connected to a collection vessel (2) with fluid line and gas equalizing line. Charging the extractor (1) with material is done through a valve (7).

The material front loading on horizontal vessel may be done by the perforated basket. When closing the front (7) the raw material is loaded and extractor (1) is hermetically sealed. After the extraction, the miscella is drained to the cooler (11) via pipe and ball valve (8). The whole vessel may be insulated for improving the heat exchange.

Cooler/Decanter 2 is a vertical cylindrical vessel that is used for cooling the resulting miscella and its degreasing of the lipophilic fraction by decanting. The total volume is 5.6 liter and it is located in the lower part of the system under the extractor (1) in order to ensure a gravity flow of the heated miscella to the cooler (2). The cooler (2) is connected to the extractor (1) by a liquid supply line and to the air pressure bottle (3) or/and extractor (1) with gas equalizing line.

Cooling is accomplished by cooling jacket mounted around the main casing cooled by a cooling fluid (11). For this purpose, the coolant is water, or an alternative may be used. The water cooling part may be equipped with a shut-off valve and thermocouple for continuous temperature measurement. Decanted lighter oil fraction is collected in a neck at the top of the apparatus and is drawn through valve (14) while valves (15), (16) and (9) are closed. The heavier oils are drained via valve (9) when valves (14), (16) and (8) are closed. The valves are also used for internal cleaning of the apparatus after extraction. The rest of the mixture is drained from the lowest point of the device via valve (9) and additionally processed.

All the units are installed to the frame to insure a gravitational flow. An example of 5 liter bottles of pressurized gas (3) as example carbon dioxide or nitrogen may be used to provide up to 40 bar counter pressure during extraction. The tank (3) is equipped with a check valve and pressure reducing valve with maximum output overpressure of 10 bar.

Solvent Collector 4 is a cylindrical vessel that is used for storage and heating the solvent before extraction. An example volume is 7.7 liter, and in the level of filling of 80%. In this case the useful volume is about 6.0 liter. It is situated in the upper part of the system. There is a ball valve (5) to drain the hot solvent to the extractor at the bottom and equalization gas line running to the extractor (1) at the top. Furthermore, it is connected with a high pressure vessel for filling with carbon dioxide or nitrogen and a threaded sleeve (13) and a valve (5) for loading water at the top.

Heating of the solvent is done by "dry" electric heater (12) with a power rating of 800 W. The temperature of water in the vessel is regulated constantly. The collector vessel (4) also can be used as a vacuum evaporator for concentrating the miscella. The miscella is placed in the vessel (4) and is heated by open water jacket immersed in a second "dry" electric heater (12) with a power of 800 W.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

In summary, the process of the present invention can be applied to a wide variety of plants, producing various substances. The process does not require the use of plant preparation before or after introducing the material in the extractor. The process may require use of elevated heat and pressure equipment. Additional extraction steps may be added to the miscella drained from valve (9) after the process of superheated water extraction. A purification and separation stage in a case of liquid to liquid or vacuum distillation may be built as a part of the extraction process to separate some of the volatile components.

I claim:

1. An extraction system for performing an extraction of at least one constituent in a substance through an extraction fluid constituted by a subcritical fluid or a pressurized fluid, the extraction system comprising:
    an extractor for circulating the extraction fluid in said extractor under pressure and temperature conditions adequate to dissolve the at least one constituent of the substance in said extraction fluid when the substance is placed in the extractor;
    a cooler connected to the extractor for cooling the at least one constituent in said extraction fluid, wherein the cooler is located below the extractor and is connected to the extractor through a fluid line;
    heater connected to the extractor for heating the extraction fluid to a super-heated stage, wherein the heater is located above the extractor and is connected to the extractor through a fluid line; and
    a pressurized air tank connected to the extractor, the heater, and the cooler respectively through gas equalization lines for creating counter pressure;
    wherein the extraction fluid flows through the heater, the extractor, and the cooler sequentially by gravity flow.

2. The system according to claim 1, wherein said air tank is using nitrogen for said counter pressure.

3. The system according to claim 1, wherein said pressurized air tank is using carbon dioxide for said counter pressure.

4. The system according to claim 1, wherein the substance comprises light and heavy oil fractions and said cooler separates the light and heavy oil fractions.

5. The system according to claim 4, wherein said cooler is connected to a liquid to liquid countercurrent system for dissolving and separating at least one constituent in the heavy oil fraction.

6. The system according to claim 1, wherein said cooler is connected to a distillation separation system.

7. The system according to claim 5, wherein said countercurrent system is connected to a separator for separating at least one constituent in the heavy oil fraction.

8. The system according to claim 1, further comprising a supporting frame having an upper part, a middle part, and a lower part, wherein the heater is located in the upper part, the extractor is located in the middle part, and the cooler is located in the lower part.

9. The system according to claim 1, wherein the extractor, the cooler, and the heater are cylindrical vessels.

10. The system according to claim 1, wherein the heater further comprises a dry electric heater.

11. The system according to claim 1, wherein the extraction fluid is water.

12. The system according to claim 1, wherein the extractor comprises a total volume of 2.6 L and a useful volume of 1.7 L, the cooler comprises a total volume of 5.6 L, and the heater comprises a volume of 6.0 L.

13. The system according to claim 1, wherein the extractor further comprises a perforated basket for loading the substance.

* * * * *